United States Patent [19]
Sheppard

[11] Patent Number: 6,153,420
[45] Date of Patent: Nov. 28, 2000

[54] SERINE PROTEASE POLYPEPTIDES AND MATERIALS AND METHODS FOR MAKING THEM

[75] Inventor: Paul O. Sheppard, Redmond, Wash.

[73] Assignee: ZymoGenetics, Inc., Seattle, Wash.

[21] Appl. No.: 09/072,384

[22] Filed: May 4, 1998

Related U.S. Application Data

[63] Continuation-in-part of application No. 09/062,142, Apr. 17, 1998, abandoned.
[60] Provisional application No. 60/044,185, Apr. 24, 1997.
[51] Int. Cl.[7] .............................. C12N 9/64; C12N 15/57; C12N 15/62; C12N 15/70; C12N 15/79
[52] U.S. Cl. .................. 435/226; 435/69.1; 435/69.7; 435/252.3; 435/25.33; 435/320.1; 435/417; 536/23.2; 536/23.4
[58] Field of Search ................... 435/226, 69.1, 435/69.7, 252.3, 252.33, 320.1, 417; 536/23.2, 23.4

[56] References Cited

U.S. PATENT DOCUMENTS

| | | | |
|---|---|---|---|
| 5,460,950 | 10/1995 | Barr et al. | 435/69.1 |
| 5,460,953 | 10/1995 | Gerlitz et al. | 435/226 |
| 5,804,410 | 9/1998 | Yamaoka et al. | 435/69.1 |
| 5,863,756 | 1/1999 | Barr et al. | 435/69.1 |

FOREIGN PATENT DOCUMENTS

95/14772  6/1965  WIPO .

OTHER PUBLICATIONS

Li, k., et al., GenBank nucleotide sequence Accession No. AF015287, "A novel serine protease from human umbilical vein endothelial cells, clone 10.16", 1997.
Clone ID 3655371, Incyte Pharmaceuticals, Inc., Oct. 6, 1997.
Clone ID 3655384, Incyte Pharmaceuticals, Inc., Oct. 6, 1997.
Clone ID 3656369, Incyte Pharmaceuticals, Inc., Oct. 6, 1997.
LIFESEQ™ Clone Information Results, Incyte Pharmaceuticals, Inc., 1995.
LIFESEQ™ Clone Information Results, Incyte Pharmaceuticals, Inc., 1995.
LIFESEQ™ Clone Information Results, Incyte Pharmaceuticals, Inc., 1995.
LIFESEQ™ Clone Information Results, Incyte Pharmaceuticals, Inc., 1995.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1996.
LIFESEQ™ Clone Information Results, Incyte Pharmaceuticals, Inc., 1997.
LIFESEQ™ Clone Information Results, Incyte Pharmaceuticals, Inc., 1997.
LIFESEQ™ Clone Information Results, Incyte Pharmaceuticals, Inc., 1997.
LIFESEQ™ Clone Information Results, Incyte Pharmaceuticals, Inc., 1997.
LIFESEQ™ Clone Information Results, Incyte Pharmaceuticals, Inc., 1997.

(List continued on next page.)

*Primary Examiner*—Ponnathapu Achutamurthy
*Assistant Examiner*—William W. Moore
*Attorney, Agent, or Firm*—Gary E. Parker

[57] ABSTRACT

A novel serine protease is disclosed. The protease comprises a sequence of amino acid residues that is at least 95% identical to SEQ ID NO:2 from Ile, residue 111, through Asn, residue 373. Also disclosed are polynucleotide molecules encoding the protease, expression vectors containing the polynucleotides, cultured cells containing the expression vectors, and methods of making the protease. The protease can be used, inter alia, within industrial processes to degrade unwanted proteins or alter the characteristics of protein-containing compositions.

24 Claims, No Drawings

OTHER PUBLICATIONS

LIFESEQ™ Clone Information Results, Incyte Pharmaceuticals, Inc., 1997.

(repeated entry appears many times on page)

LIFESEQ™ Clone Information Results, Incyte Pharmaceuticals, Inc., 1997.

LIFESEQ™ Clone Information Results, Incyte Pharmaceuticals, Inc., 1997.

LIFESEQ™ Clone Information Results, Incyte Pharmaceuticals, Inc., 1997.

LIFESEQ™ Clone Information Results, Incyte Pharmaceuticals, Inc., 1997.

LIFESEQ™ Clone Information Results, Incyte Pharmaceuticals, Inc., 1997.

LIFESEQ™ Clone Information Results, Incyte Pharmaceuticals, Inc., 1997.

LIFESEQ™ Clone Information Results, Incyte Pharmaceuticals, Inc., 1997.

Marra et al., The Wash U–Merck EST Project, 1996.

Marra et al., The Wash U–Merck EST Project, 1996.

Hillier et al., The Wash U–Merck EST Project, 1997.

Marra et al., The Wash U–Merck EST Project, 1996.

Hillier et al., The Wash U–Merck EST Project, 1995.

Hillier et al., The Wash U–Merck EST Project, 1995.

Adams et al., Institute for Genomic Research, 1995.

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 1634 base pairs
      (B) TYPE: nucleic acid
      (C) STRANDEDNESS: double
      (D) TOPOLOGY: linear (ix) FEATURE:
      (A) NAME/KEY: Coding Sequence
      (B) LOCATION: 105...1280
      (D) OTHER INFORMATION:
      (A) NAME/KEY: Signal Sequence
      (B) LOCATION: 105...161
      (D) OTHER INFORMATION:

(xi) SEQUENCE DESCRIPTION: SEQ ID NO:1:

```
GGCACGAGGG GGAGCCGCGC GCTCTCTCCC GGCGCCCACA CCTGTCTGAG CGGCGCAGCG         60

AGCCGCGGCC CGGGCGGGCT GCTCGGCGCG AACAGTGCT CGGC ATG GCA GGG ATT         116
                                                Met Ala Gly Ile

CCA GGG CTC CTC TTC CTT CTC TTC TTT CTG CTC TGT GCT GTT GGG CAA         164
Pro Gly Leu Leu Phe Leu Leu Phe Phe Leu Leu Cys Ala Val Gly Gln
-15              -10                 -5                        1

GTG AGC CCT TAC AGT GCC CCC TGG AAA CCC ACT TGG CCT GCA TAC CGC         212
Val Ser Pro Tyr Ser Ala Pro Trp Lys Pro Thr Trp Pro Ala Tyr Arg
              5                  10                 15

CTC CCT GTC GTC TTG CCC CAG TCT ACC CTC AAT TTA GCC AAG CCA GAC         260
Leu Pro Val Val Leu Pro Gln Ser Thr Leu Asn Leu Ala Lys Pro Asp
             20                  25                  30

TTT GGA GCC GAA GCC AAA TTA GAA GTA TCT TCT TCA TGT GGA CCC CAG         308
```

```
Phe Gly Ala Glu Ala Lys Leu Glu Val Ser Ser Cys Gly Pro Gln
 35                  40                  45

GT  CAT AAG GGA ACT CCA CTG CCC ACT TAC AAA GAA GCC AAG CAA TAT        356
    Cys His Lys Gly Thr Pro Leu Pro Thr Tyr Lys Glu Ala Lys Gln Tyr
    50                  55                  60                  65

CTG TCT TAT GAA ACG CTC TAT GCC AAT GGC AGC CGC ACA GAG ACN CAG        404
Leu Ser Tyr Glu Thr Leu Tyr Ala Asn Gly Ser Arg Thr Glu Xaa Gln
                70                  75                  80

GTG GGC ATC TAC ATC CTC AGC AGT AGT GGA GAT GGG GCC CAN CNC CGA        452
Val Gly Ile Tyr Ile Leu Ser Ser Ser Gly Asp Gly Ala Xaa Xaa Arg
            85                  90                  95

GAC TCA GGG TCT TCA GGA AAG TCT CGA AGG AAG CGG CAG ATT TAT GGC        500
Asp Ser Gly Ser Ser Gly Lys Ser Arg Arg Lys Arg Gln Ile Tyr Gly
        100                 105                 110

TAT GAC AGC AGG TTC AGC ATT TTT GGG AAG GAC TTC CTG CTC AAC TAC        548
Tyr Asp Ser Arg Phe Ser Ile Phe Gly Lys Asp Phe Leu Leu Asn Tyr
    115                 120                 125

CCT TTC TCA ACA TCA GTG AAG TTA TCC ACG GGC TGC ACC GGC ACC CTG        596
Pro Phe Ser Thr Ser Val Lys Leu Ser Thr Gly Cys Thr Gly Thr Leu
130                 135                 140                 145

GTG GCA GAA AAN CAT GTC CTC ACA GCT GCC CAC TGC ATA CAC GAT GGA        644
Val Ala Glu Xaa His Val Leu Thr Ala Ala His Cys Ile His Asp Gly
                150                 155                 160

AAA ACC TAT GTG AAA GGA ACC CAG AAG CTT CGA GTC GGC TTC CTA AAG        692
Lys Thr Tyr Val Lys Gly Thr Gln Lys Leu Arg Val Gly Phe Leu Lys
            165                 170                 175

CCC AAG TTT AAA GAT GGT GGT CGA GGG GCC AAC GAC TCC ACT TCA GCC        740
Pro Lys Phe Lys Asp Gly Gly Arg Gly Ala Asn Asp Ser Thr Ser Ala
        180                 185                 190

ATG CCC GAG CAG ATG AAA TTT CAG TGG ATC CGG GTG AAA CGC ACC CAT        788
Met Pro Glu Gln Met Lys Phe Gln Trp Ile Arg Val Lys Arg Thr His
    195                 200                 205

GTG CCC AAG GGT TGG ATC AAG GGC AAT GCC AAT GAC ATC GGC ATG GAT        836
Val Pro Lys Gly Trp Ile Lys Gly Asn Ala Asn Asp Ile Gly Met Asp
210                 215                 220                 225

TAT GAT TAT GCC CTC CTG GAA CTC AAA AAG CCC CAC AAG AGA AAA TTT        884
Tyr Asp Tyr Ala Leu Leu Glu Leu Lys Lys Pro His Lys Arg Lys Phe
                230                 235                 240

ATG AAG ATT GGG GTG AGC CCT CCT GCT AAG CAG CTG CCA GGG GGC AGA        932
Met Lys Ile Gly Val Ser Pro Pro Ala Lys Gln Leu Pro Gly Gly Arg
            245                 250                 255

ATT CAC TTC TCT GGT TAT GAC AAT GAC CGA CCA GGC AAT TTG GTG TAT        980
Ile His Phe Ser Gly Tyr Asp Asn Asp Arg Pro Gly Asn Leu Val Tyr
        260                 265                 270

CGC TTC TGT GAC GTC AAA GAC GAG ACC TAT GAC TTG TTG TAC CAG CAA       1028
Arg Phe Cys Asp Val Lys Asp Glu Thr Tyr Asp Leu Leu Tyr Gln Gln
    275                 280                 285

TGC GAT GCC CAG CCA GGG GCC AGC GGG TAT GGG GTA TAT GTG AGG ATG       1076
Cys Asp Ala Gln Pro Gly Ala Ser Gly Tyr Gly Val Tyr Val Arg Met
290                 295                 300                 305

TGG AAG AGA CAG CAG CAG AAG TGG GAG CGA AAA ATT ATT GGC ATT TTT       1124
Trp Lys Arg Gln Gln Gln Lys Trp Glu Arg Lys Ile Ile Gly Ile Phe
                310                 315                 320

TCA GGG CAC CAG TGG GTG GAC ATG AAT GGT TCC CCA CAG GAT TTC AAC       1172
Ser Gly His Gln Trp Val Asp Met Asn Gly Ser Pro Gln Asp Phe Asn
            325                 330                 335

GTG GCT GTC AGA ATC ACT CCT CTC AAA TAT GCC CAG ATC TGC TAT TGG       1220
Val Ala Val Arg Ile Thr Pro Leu Lys Tyr Ala Gln Ile Cys Tyr Trp
        340                 345                 350
```

```
ATT AAA GGA AAC TAC CTG GAT TGT AGG GAG GGT GAC ACA GTG TTC CTT      1268
Ile Lys Gly Asn Tyr Leu Asp Cys Arg Glu Gly Asp Thr Val Phe Leu
    355                 360                 365

CCT GGC AGC AAT TAAGGTCTTC ATGTTCTTAT TTTAGGAGAG GCCAAATTGT TTTTT     1325
Pro Gly Ser Asn
370

GTCATTGGCG TGCACACGTG TGTGTGTGTG TGTGTGTGTG TGTAAGGTGT CTTATAATCT    1385

TTTACCTATT TCTTACAATT GCAAGATGAC TGGCTTTACT ATTTGAAAAC TGGTTTGTGT    1445

ATCATATCAT ATATCATTTA AGCAGTTTGA AGGCATACTT TTGCATAGAA ATAAAAAAAA    1505

TACTGATTTG GGGCAATGAG GAATATTTGA CAATTAAGTT AATCTTCACG TTTTTGCAAA    1565

CTTTGATTTT TATTTCATCT GAACTTGTTT CAAAGATTTA TATTAAATAT TTGGCATACA    1625

AGAGATATG                                                              1634

(2) INFORMATION FOR SEQ ID NO:2:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:2:

Met Ala Gly Ile Pro Gly Leu Leu Phe Leu Leu Phe Leu Leu Cys
                -15                 -10                 -5

Ala Val Gly Gln Val Ser Pro Tyr Ser Ala Pro Trp Lys Pro Thr Trp
                1               5                   10

Pro Ala Tyr Arg Leu Pro Val Val Leu Pro Gln Ser Thr Leu Asn Leu
            15                  20                  25

Ala Lys Pro Asp Phe Gly Ala Glu Ala Lys Leu Glu Val Ser Ser Ser
30                  35                  40                  45

Cys Gly Pro Gln Cys His Lys Gly Thr Pro Leu Pro Thr Tyr Lys Glu
                50                  55                  60

Ala Lys Gln Tyr Leu Ser Tyr Gly Thr Leu Tyr Ala Asn Gly Ser Arg
            65                  70                  75

Thr Glu Xaa Gln Val Gly Ile Tyr Ile Leu Ser Ser Gly Asp Gly
        80                  85                  90

Ala Xaa Xaa Arg Asp Ser Gly Ser Ser Gly Lys Ser Arg Arg Lys Arg
    95                  100                 105

Gln Ile Tyr Gly Tyr Asp Ser Arg Phe Ser Ile Phe Gly Lys Asp Phe
110                 115                 120                 125

Leu Leu Asn Tyr Pro Phe Ser Thr Ser Val Lys Leu Ser Thr Gly Cys
                130                 135                 140

Thr Gly Thr Leu Val Ala Glu Xaa His Val Leu Thr Ala Ala His Cys
            145                 150                 155

Ile His Asp Gly Lys Thr Tyr Val Lys Gly Thr Gln Lys Leu Arg Val
            160                 165                 170

Gly Phe Leu Lys Pro Lys Phe Lys Asp Gly Gly Arg Gly Ala Asn Asp
            175                 180                 185
```

```
Ser Thr Ser Ala Met Pro Glu Gln Met Lys Phe Gln Trp Ile Arg Val
190                 195                 200                 205

Lys Arg Thr His Val Pro Lys Gly Trp Ile Lys Gly Asn Ala Asn Asp
                210                 215                 220

Ile Gly Met Asp Tyr Asp Tyr Ala Leu Leu Glu Leu Lys Lys Pro His
                225                 230                 235

Lys Arg Lys Phe Met Lys Ile Gly Val Ser Pro Pro Ala Lys Gln Leu
                240                 245                 250

Pro Gly Gly Arg Ile His Phe Ser Gly Tyr Asp Asn Asp Arg Pro Gly
255                 260                 265

Asn Leu Val Tyr Arg Phe Cys Asp Val Lys Asp Glu Thr Tyr Asp Leu
270                 275                 280                 285

Leu Tyr Gln Gln Cys Asp Ala Gln Pro Gly Ala Ser Gly Tyr Gly Val
                290                 295                 300

Tyr Val Arg Met Trp Lys Arg Gln Gln Lys Trp Glu Arg Lys Ile
                305                 310                 315

Ile Gly Ile Phe Ser Gly His Gln Trp Val Asp Met Asn Gly Ser Pro
                320                 325                 330

Gln Asp Phe Asn Val Ala Val Arg Ile Thr Pro Leu Lys Tyr Ala Gln
                335                 340                 345

Ile Cys Tyr Trp Ile Lys Gly Asn Tyr Leu Asp Cys Arg Glu Gly Asp
350                 355                 360                 365

Thr Val Phe Leu Pro Gly Ser Asn
                370

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:3:

TGYACNGGNW SNHTNRT                                                      17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

AYNADNSWNC CNGTRCA                                                      17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:5:

ACNGCNGSNC AYTGYAT                                                      17

(2) INFORMATION FOR SEQ ID NO:6:

(i) SEQUENCE CHARACTERISTICS:
```

```
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:6:

ATRCARTGNS CNGCNGT                                              17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:7:

WYRTNCCNWV NGGNTGG                                              17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:8:

CCANCCNBWN GGNAYRW                                              17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

AYNRAYTAYG AYTAYGS                                              17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

SCRTARTCRT ARTYNRT                                              17

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC11667

(xi) SEQUENCE DESCRIPTION: SEQ ID NO:11:

TATGCAGGCC AAGTGGGTTT CCAGGGGGCA CTGTAAGGGC                      40
```

-continued (2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13508

(xi) SEQUENCE DESCRIPTION: SEQ ID NO:12:

```
TCTGCTCTGT GCTGTTGG                                              18
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13509

(xi) SEQUENCE DESCRIPTION: SEQ ID NO:13:

```
AGTCTGGCTT GGCTAAAT                                              18
```

(2) INFORMATION FOR SEQ ID NO:14:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 105...1280
        (D) OTHER INFORMATION:
        (A) NAME/KEY: Signal Sequence
        (B) LOCATION: 105...161
        (D) OTHER INFORMATION:

(xi) SEQUENCE DESCRIPTION: SEQ ID NO:14:

```
GGCACGAGGG GGAGCCGCGC GCTCTCTCCC GGCGCCCACA CCTGTCTGAG CGGCGCAGCG      60
AGCCGCGGCC CGGGCGGGCT GCTCGGCGCG AACAGTGCT CGGC ATG GCA GGG ATT      116
                                              Met Ala Gly Ile

CCA GGG CTC CTC TTC CTT CTC TTC TTT CTG CTC TGT GCT GTT GGG CAA      164
Pro Gly Leu Leu Phe Leu Leu Phe Phe Leu Leu Cys Ala Val Gly Gln
-15                 -10                 -5                   1

GTG AGC CCT TAC AGT GCC CCC TGG AAA CCC ACT TGG CCT GCA TAC CGC      212
Val Ser Pro Tyr Ser Ala Pro Trp Lys Pro Thr Trp Pro Ala Tyr Arg
            5                   10                  15

CTC CCT GTC GTC TTG CCC CAG TCT ACC CTC AAT TTA GCC AAG CCA GAC      260
Leu Pro Val Val Leu Pro Gln Ser Thr Leu Asn Leu Ala Lys Pro Asp
        20                  25                  30

TTT GGA GCC GAA GCC AAA TTA GAA GTA TCT TCT TCA TGT GGA CCC CAG      308
Phe Gly Ala Glu Ala Lys Leu Glu Val Ser Ser Ser Cys Gly Pro Gln
    35                  40                  45

TGT CAT AAG GGA ACT CCA CTG CCC ACT TAC GAA GAG GCC AAG CAA TAT      356
Cys His Lys Gly Thr Pro Leu Pro Thr Tyr Glu Glu Ala Lys Gln Tyr
```

-continued

```
50                       55                       60                       65
CTG TCT TAT GAA ACG CTC TAT GCC AAT GGC AGC CGC ACA GAG ACG CAG              404
Leu Ser Tyr Glu Thr Leu Tyr Ala Asn Gly Ser Arg Thr Glu Thr Gln
                    70                       75                       80

GTG GGC ATC TAC ATC CTC AGC AGT AGT GGA GAT GGG GCC CAA CAC CGA              452
Val Gly Ile Tyr Ile Leu Ser Ser Ser Gly Asp Gly Ala Gln His Arg
                85                       90                       95

GAC TCA GGG TCT TCA GGA AAG TCT CGA AGG AAG CGG CAG ATT TAT GGC              500
Asp Ser Gly Ser Ser Gly Lys Ser Arg Arg Lys Arg Gln Ile Tyr Gly
            100                      105                      110

TAT GAC AGC AGG TTC AGC ATT TTT GGG AAG GAC TTC CTG CTC AAC TAC              548
Tyr Asp Ser Arg Phe Ser Ile Phe Gly Lys Asp Phe Leu Leu Asn Tyr
        115                      120                      125

CCT TTC TCA ACA TCA GTG AAG TTA TCC ACG GGC TGC ACC GGC ACC CTG              596
Pro Phe Ser Thr Ser Val Lys Leu Ser Thr Gly Cys Thr Gly Thr Leu
130                      135                      140                      145

GTG GCA GAG AAG CAT GTC CTC ACA GCT GCC CAC TGC ATA CAC GAT GGA              644
Val Ala Glu Lys His Val Leu Thr Ala Ala His Cys Ile His Asp Gly
                150                      155                      160

AAA ACC TAT GTG AAA GGA ACC CAG AAG CTT CGA GTG GGC TTC CTA AAG              692
Lys Thr Tyr Val Lys Gly Thr Gln Lys Leu Arg Val Gly Phe Leu Lys
                165                      170                      175

CCC AAG TTT AAA GAT GGT GGT CGA GGG GCC AAC GAC TCC ACT TCA GCC              740
Pro Lys Phe Lys Asp Gly Gly Arg Gly Ala Asn Asp Ser Thr Ser Ala
            180                      185                      190

ATG CCC GAG CAG ATG AAA TTT CAG TGG ATC CGG GTG AAA CGC ACC CAT              788
Met Pro Glu Gln Met Lys Phe Gln Trp Ile Arg Val Lys Arg Thr His
195                      200                      205

GTG CCC AAG GGT TGG ATC AAG GGC AAT GCC AAT GAC ATC GGC ATG GAT              836
Val Pro Lys Gly Trp Ile Lys Gly Asn Ala Asn Asp Ile Gly Met Asp
210                      215                      220                      225

TAT GAT TAT GCC CTC CTG GAA CTC AAA AAG CCC CAC AAG AGA AAA TTT              884
Tyr Asp Tyr Ala Leu Leu Glu Leu Lys Lys Pro His Lys Arg Lys Phe
                230                      235                      240

ATG AAG ATT GGG GTG AGC CCT CCT GCT AAG CAG CTG CCA GGG GGC AGA              932
Met Lys Ile Gly Val Ser Pro Pro Ala Lys Gln Leu Pro Gly Gly Arg
                245                      250                      255

ATT CAC TTC TCT GGT TAT GAC AAT GAC CGA CCA GGC AAT TTG GTG TAT              980
Ile His Phe Ser Gly Tyr Asp Asn Asp Arg Pro Gly Asn Leu Val Tyr
            260                      265                      270

CGC TTC TGT GAC GTC AAA GAC GAG ACC TAT GAC TTG CTC TAC CAG CAA             1028
Arg Phe Cys Asp Val Lys Asp Glu Thr Tyr Asp Leu Leu Tyr Gln Gln
        275                      280                      285

TGC GAT GCC CAG CCA GGG GCC AGC GGG TCT GGG GTC TAT GTG AGG ATG             1076
Cys Asp Ala Gln Pro Gly Ala Ser Gly Ser Gly Val Tyr Val Arg Met
290                      295                      300                      305

TGG AAG AGA CAG CAG CAG AAG TGG GAG CGA AAA ATT ATT GGC ATT TTT             1124
Trp Lys Arg Gln Gln Gln Lys Trp Glu Arg Lys Ile Ile Gly Ile Phe
                310                      315                      320

TCA GGG CAC CAG TGG GTG GAC ATG AAT GGT TCC CCA CAG GAT TTC AAC             1172
Ser Gly His Gln Trp Val Asp Met Asn Gly Ser Pro Gln Asp Phe Asn
            325                      330                      335

GTG GCT GTC AGA ATC ACT CCT CTC AAA TAT GCC CAG ATC TGC TAT TGG             1220
Val Ala Val Arg Ile Thr Pro Leu Lys Tyr Ala Gln Ile Cys Tyr Trp
        340                      345                      350

ATT AAA GGA AAC TAC CTG GAT TGT AGG GAG GGT GAC ACA GTG TTC CCT             1268
Ile Lys Gly Asn Tyr Leu Asp Cys Arg Glu Gly Asp Thr Val Phe Pro
355                      360                      365

CCT GGC AGC AAT TAAGGTCTTC ATGTTCTTAT TTAGGAGAG GCCAAATTGT TTTTT            1325
Pro Gly Ser Asn
```

```
Pro Gly Ser Asn
370

GTCATTGGCG TGCACACGTG TGTGTGTGTG TGTGTGTGTG TGTAAGGTGT CTTATAATCT      1385

TTTACCTATT TCTTACAATT GCAAGATGAC TGGCTTTACT ATTTGAAAAC TGGTTTGTGT      1445

ATCATATCAT ATATCATTTA AGCAGTTTGA AGGCATACTT TTGCATAGAA ATAAAAAAAA      1505

TACTGATTTG GGGCAATGAG GAATATTTGA CAATTAAGTT AATCTTCACG TTTTTGCAAA      1565

CTTTGATTTT TATTTCATCT GAACTTGTTT CAAAGATTTA TATTAAATAT TTGGCATACA      1625

AGAGATATGA AAAAAAAAAA AAAAAAAAA A                                     1656

(2) INFORMATION FOR SEQ ID NO:15:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:15:

Met Ala Gly Ile Pro Gly Leu Leu Phe Leu Leu Phe Phe Leu Leu Cys
                -15                 -10                  -5

Ala Val Gly Gln Val Ser Pro Tyr Ser Ala Pro Trp Lys Pro Thr Trp
                 1               5                  10

Pro Ala Tyr Arg Leu Pro Val Val Leu Pro Gln Ser Thr Leu Asn Leu
             15                  20                  25

Ala Lys Pro Asp Phe Gly Ala Glu Ala Lys Leu Glu Val Ser Ser Ser
30                  35                  40                  45

Cys Gly Pro Gln Cys His Lys Gly Thr Pro Leu Pro Thr Tyr Glu Glu
                50                  55                  60

Ala Lys Gln Tyr Leu Ser Tyr Glu Thr Leu Tyr Ala Asn Gly Ser Arg
                65                  70                  75

Thr Glu Thr Gln Val Gly Ile Tyr Ile Leu Ser Ser Gly Asp Gly
                80                  85                  90

Ala Gln His Arg Asp Ser Gly Ser Ser Gly Lys Ser Arg Arg Lys Arg
    95                  100                 105

Gln Ile Tyr Gly Tyr Asp Ser Arg Phe Ser Ile Phe Gly Lys Asp Phe
110                 115                 120                 125

Leu Leu Asn Tyr Pro Phe Ser Thr Ser Val Lys Leu Ser Thr Gly Cys
                130                 135                 140

Thr Gly Thr Leu Val Ala Glu Lys His Val Leu Thr Ala Ala His Cys
                145                 150                 155

Ile His Asp Gly Lys Thr Tyr Val Lys Gly Thr Gln Lys Leu Arg Val
                160                 165                 170

Gly Phe Leu Lys Pro Lys Phe Lys Asp Gly Gly Arg Gly Ala Asn Asp
                175                 180                 185

Ser Thr Ser Ala Met Pro Glu Gln Met Lys Phe Gln Trp Ile Arg Val
190                 195                 200                 205

Lys Arg Thr His Val Pro Lys Gly Trp Ile Lys Gly Asn Ala Asn Asp
                210                 215                 220
```

```
Ile Gly Met Asp Tyr Asp Tyr Ala Leu Leu Glu Leu Lys Lys Pro His
            225                 230                 235

Lys Arg Lys Phe Met Lys Ile Gly Val Ser Pro Ala Lys Gln Leu
        240                 245                 250

Pro Gly Gly Arg Ile His Phe Ser Gly Tyr Asp Asn Asp Arg Pro Gly
        255                 260                 265

Asn Leu Val Tyr Arg Phe Cys Asp Val Lys Asp Glu Thr Tyr Asp Leu
270                 275                 280                 285

Leu Tyr Gln Gln Cys Asp Ala Gln Pro Gly Ala Ser Gly Ser Gly Val
                290                 295                 300

Tyr Val Arg Met Trp Lys Arg Gln Gln Lys Trp Glu Arg Lys Ile
                305                 310                 315

Ile Gly Ile Phe Ser Gly His Gln Trp Val Asp Met Asn Gly Ser Pro
            320                 325                 330

Gln Asp Phe Asn Val Ala Val Arg Ile Thr Pro Leu Lys Tyr Ala Gln
            335                 340                 345

Ile Cys Tyr Trp Ile Lys Gly Asn Tyr Leu Asp Cys Arg Glu Gly Asp
350                 355                 360                 365

Thr Val Phe Pro Pro Gly Ser Asn
                370
```

(2) INFORMATION FOR SEQ ID NO:16:

(i) SEQUENCE CHARACTERISTICS:
        (A) LENGTH: 1176 base pairs
        (B) TYPE: nucleic acid
        (C) STRANDEDNESS: single
        (D) TOPOLOGY: linear (xi) SEQUENCE DESCRIPTION: SEQ ID NO:16:

```
ATGGCNGGNA THCCNGGNYT NYTNTTYYTN YTNTTYTTYY TNYTNTGYGC NGTNGGNCAR      60

GTNWSNCCNT AYWSNGCNCC NTGGAARCCN ACNTGGCCNG CNTAYMGNYT NCCNGTNGTN     120

YTNCCNCARW SNACNYTNAA YYTNGCNAAR CCNGAYTTYG GNGCNGARGC NAARYTNGAR     180

GTNWSNWSNW SNTGYGGNCC NCARTGYCAY AARGGNACNC CNYTNCCNAC NTAYGARGAR     240

GCNAARCART AYYTNWSNTA YGARACNYTN TAYGCNAAYG GNWSNMGNAC NGARACNCAR     300

GTNGGNATHT AYATHYTNWS NWSNWSNGGN GAYGGNGCNC ARCAYMGNGA YWSNGGNWSN     360

WSNGGNAARW SNMGNMGNAA RMGNCARATH TAYGGNTAYG AYWSNMGNTT YWSNATHTTY     420

GGNAARGAYT TYYTNYTNAA YTAYCCNTTY WSNACNWSNG TNAARYTNWS NACNGGNTGY     480

ACNGGNACNY TNGTNGCNGA RAARCAYGTN YTNACNGCNG CNCAYTGYAT HCAYGAYGGN     540

AARACNTAYG TNAARGGNAC NCARAARYTN MGNGTNGGNT TYYTNAARCC NAARTTYAAR     600

GAYGGNGGNM GNGGNGCNAA YGAYWSNACN WSNGCNATGC CNGARCARAT GAARTTYCAR     660

TGGATHMGNG TNAARMGNAC NCAYGTNCCN AARGGNTGGA THAARGGNAA YGCNAAYGAY     720

ATHGGNATGG AYTAYGAYTA YGCNYTNYTN GARYTNAARA ARCCNCAYAA RMGNAARTTY     780

ATGAARATHG GNGTNWSNCC NCCNGCNAAR CARYTNCCNG GNGGNMGNAT HCAYTTYWSN     840

GGNTAYGAYA AYGAYMGNCC NGGNAAYYTN GTNTAYMGNT TYTGYGAYGT NAARGAYGAR     900

ACNTAYGAYY TNYTNTAYCA RCARTGYGAY GCNCARCCNG GNGCNWSNGG NWSNGGNGTN     960

TAYGTNMGNA TGTGGAARMG NCARCARCAR AARTGGGARM GNAARATHAT HGGNATHTTY    1020

WSNGGNCAYC ARTGGGTNGA YATGAAYGGN WSNCCNCARG AYTTYAAYGT NGCNGTNMGN    1080

ATHACNCCNY TNAARTAYGC NCARATHTGY TAYTGGATHA ARGGNAAYTA YYTNGAYTGY    1140
```

MGNGARGGNG AYACNGTNTT YCCNCCNGGN WSNAAY                                         1176

(2) INFORMATION FOR SEQ ID NO:17:

(i) SEQUENCE CHARACTERISTICS:
        (A) LENGTH: 1679 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 111...1259
        (D) OTHER INFORMATION:
        (A) NAME/KEY: Signal Sequence
        (B) LOCATION: 111...167
        (D) OTHER INFORMATION:

(xi) SEQUENCE DESCRIPTION: SEQ ID NO:17:

GAATTCGGCA CGAGGGGGAG CCGCGCGCTC TCTCCCGGCG CCCACACCTG TCTGAGCGGC          60

GCAGCGAGCC GCGGCCCGGG CGGGCTGCTC GGCGCGGAAC AGTGCTCGGC ATG GCA            116
                                                         Met Ala

GGG ATT CCA GGG CTC CTC TTC CTT CTC TTC TTT CTG CTC TGT GCT GTT            164
Gly Ile Pro Gly Leu Leu Phe Leu Leu Phe Phe Leu Leu Cys Ala Val
        -15             -10                 -5

GGG CAA GTG AGC CCT TAC AGT GCC CCC TGG AAA CCC ACT TGG CCT GCA            212
Gly Gln Val Ser Pro Tyr Ser Ala Pro Trp Lys Pro Thr Trp Pro Ala
    1             5                  10                  15

TAC CGC CTC CCT GTC GTC TTG CCC CAG TCT ACC CTC AAT TTA GCC AAG            260
Tyr Arg Leu Pro Val Val Leu Pro Gln Ser Thr Leu Asn Leu Ala Lys
                20              25              30

CCA GAC TTT GGA GCC GAA GCC AAA TTA GAA GTA TCT TCT TCA TGT GGA            308
Pro Asp Phe Gly Ala Glu Ala Lys Leu Glu Val Ser Ser Ser Cys Gly
            35              40              45

CCC CAG TGT CAT AAG GGA ACT CCA CTG CCC ACT TAC GAA GAG GCC AAG            356
Pro Gln Cys His Lys Gly Thr Pro Leu Pro Thr Tyr Glu Glu Ala Lys
        50              55              60

CAA TAT CTG TCT TAT GAA ACG CTC TAT GCC AAT GGC AGC CGC ACA GAG            404
Gln Tyr Leu Ser Tyr Glu Thr Leu Tyr Ala Asn Gly Ser Arg Thr Glu
65              70              75

ACG CAG GTG GGC ATC TAC ATC CTC AGC AGT AGT GGA GAT GGG GCC CAA            452
Thr Gln Val Gly Ile Tyr Ile Leu Ser Ser Ser Gly Asp Gly Ala Gln
80              85              90              95

CAC CGA GAC TCA GGG TCT TCA GGA AAG TCT CGA AGG AAG CGG CAG ATT            500
His Arg Asp Ser Gly Ser Ser Gly Lys Ser Arg Arg Lys Arg Gln Ile
            100             105             110

TAT GGC TAT GAC AGC AGG TTC AGC ATT TTT GGG AAG GAC TTC CTG CTC            548
Tyr Gly Tyr Asp Ser Arg Phe Ser Ile Phe Gly Lys Asp Phe Leu Leu
        115             120             125

AAC TAC CCT TTC TCA ACA TCA GTG AAG TTA TCC ACG GGC TGC ACC GGC            596
Asn Tyr Pro Phe Ser Thr Ser Val Lys Leu Ser Thr Gly Cys Thr Gly
    130             135             140

ACC CTG GTG GCA GAG AAG CAT GTC CTC ACA GCT GCC CAC TGC ATA CAC            644
Thr Leu Val Ala Glu Lys His Val Leu Thr Ala Ala His Cys Ile His
        145             150             155

GAT GGA AAA ACC TAT GTG AAA GGA ACC CAG AAG CTT CGA GTG GGC TTC            692
Asp Gly Lys Thr Tyr Val Lys Gly Thr Gln Lys Leu Arg Val Gly Phe
160             165             170             175

CTA AAG CCC AAG TTT AAA GAT GGT GGT CGA GGG GCC AAC GAC TCC ACT            740
Leu Lys Pro Lys Phe Lys Asp Gly Gly Arg Gly Ala Asn Asp Ser Thr
            180             185             190

-continued

```
TCA GCC ATG CCC GAG CAG ATG AAA TTT CAG TGG ATC CGG GTG AAA CGC      788
Ser Ala Met Pro Glu Gln Met Lys Phe Gln Trp Ile Arg Val Lys Arg
        195                 200                 205

ACC CAT GTG CCC AAG GGT TGG ATC AAG GGC AAT GCC AAT GAC ATC GGC      836
Thr His Val Pro Lys Gly Trp Ile Lys Gly Asn Ala Asn Asp Ile Gly
    210                 215                 220

ATG GAT TAT GAT TAT GCC CTC CTG GAA CTC AAA AAG CCC CAC AAG AGA      884
Met Asp Tyr Asp Tyr Ala Leu Leu Glu Leu Lys Lys Pro His Lys Arg
225                 230                 235

AAA TTT ATG AAG ATT GGG GTG AGC CCT CCT GCT AAG CAG CTG CCA GGG      932
Lys Phe Met Lys Ile Gly Val Ser Pro Pro Ala Lys Gln Leu Pro Gly
240                 245                 250                 255

GGC AGA ATT CAC TTC TCT GGT TAT GAC AAT GAC CGA CCA GGC AAT TTG      980
Gly Arg Ile His Phe Ser Gly Tyr Asp Asn Asp Arg Pro Gly Asn Leu
                260                 265                 270

GTG TAT CGC TTC TGT GAC GTC AAA GAC GAG ACC TAT GAC TTG CTC TAC     1028
Val Tyr Arg Phe Cys Asp Val Lys Asp Glu Thr Tyr Asp Leu Leu Tyr
            275                 280                 285

CAG CAA TGC GAT GCC CAG CCA GGG GCC AGC GGG TCT GGG GTC TAT GTG     1076
Gln Gln Cys Asp Ala Gln Pro Gly Ala Ser Gly Ser Gly Val Tyr Val
        290                 295                 300

AGG ATG TGG AAG AGA CAG CAG CAG AAG TGG GAG CGA AAA ATT ATT GGC     1124
Arg Met Trp Lys Arg Gln Gln Gln Lys Trp Glu Arg Lys Ile Ile Gly
305                 310                 315

ATT TTT TCA GGG CAC CAG TGG GTG GAC ATG AAT GGT TCC CCA CAG GAT     1172
Ile Phe Ser Gly His Gln Trp Val Asp Met Asn Gly Ser Pro Gln Asp
320                 325                 330                 335

TTC AAC GTG GCT GTC AGA ATC ACT CCT CTC AAA TAT GCC CAG ATC TGC     1220
Phe Asn Val Ala Val Arg Ile Thr Pro Leu Lys Tyr Ala Gln Ile Cys
                340                 345                 350

TAT TGG ATT AAA GGA AAC TAC CTG GAT TGT AGG GAG GGG TGACACAGTG TT   1271
Tyr Trp Ile Lys Gly Asn Tyr Leu Asp Cys Arg Glu Gly
            355                 360

CCCTCCTGGC AGCAATTAAG GGTCTTCATG TTCTTATTTT AGGAGAGGCC AAATTGTTTT   1331

TTGTCATTGG CGTGCACACG TGTGTGTGTG TGTGTGTGTG TGTGTAAGGT GTCTTATAAT   1391

CTTTTACCTA TTTCTTACAA TTGCAAGATG ACTGGCTTTA CTATTTGAAA ACTGGTTTGT   1451

GTATCATATC ATATATCATT TAAGCAGTTT GAAGGCATAC TTTTGCATAG AAATAAAAAA   1511

AATACTGATT TGGGGCAATG AGGAATATTT GACAATTAAG TTAATCTTCA CGTTTTTGCA   1571

AACTTTGATT TTTATTTCAT CTGAACTTGT TTCAAAGATT TATATTAAAT ATTTGGCATA   1631

CAAGAGATAT GAAAAAAAAA AAAAAAAAAA AAAAATTCCT GCGGCCGC               1679
```

(2) INFORMATION FOR SEQ ID NO:18:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Signal Sequence
        (B) LOCATION: 1...19
        (D) OTHER INFORMATION:

(xi) SEQUENCE DESCRIPTION: SEQ ID NO:18:

Met Ala Gly Ile Pro Gly Leu Leu Phe Leu Leu Phe Phe Leu Leu Cys

-continued

```
                -15                 -10                  -5
Ala Val Gly Gln Val Ser Pro Tyr Ser Ala Pro Trp Lys Pro Thr Trp
             1               5              10
Pro Ala Tyr Arg Leu Pro Val Leu Pro Gln Ser Thr Leu Asn Leu
 15              20              25
Ala Lys Pro Asp Phe Gly Ala Glu Ala Lys Leu Glu Val Ser Ser Ser
 30              35              40              45
Cys Gly Pro Gln Cys His Lys Gly Thr Pro Leu Pro Thr Tyr Glu Glu
             50              55              60
Ala Lys Gln Tyr Leu Ser Tyr Glu Thr Leu Tyr Ala Asn Gly Ser Arg
             65              70              75
Thr Glu Thr Gln Val Gly Ile Tyr Ile Leu Ser Ser Ser Gly Asp Gly
         80              85              90
Ala Gln His Arg Asp Ser Gly Ser Ser Gly Lys Ser Arg Arg Lys Arg
 95             100             105
Gln Ile Tyr Gly Tyr Asp Ser Arg Phe Ser Ile Phe Gly Lys Asp Phe
110             115             120             125
Leu Leu Asn Tyr Pro Phe Ser Thr Ser Val Lys Leu Ser Thr Gly Cys
             130             135             140
Thr Gly Thr Leu Val Ala Glu Lys His Val Leu Thr Ala Ala His Cys
             145             150             155
Ile His Asp Gly Lys Thr Tyr Val Lys Gly Thr Gln Lys Leu Arg Val
             160             165             170
Gly Phe Leu Lys Pro Lys Phe Lys Asp Gly Gly Arg Gly Ala Asn Asp
175             180             185
Ser Thr Ser Ala Met Pro Glu Gln Met Lys Phe Gln Trp Ile Arg Val
190             195             200             205
Lys Arg Thr His Val Pro Lys Gly Trp Ile Lys Gly Asn Ala Asn Asp
             210             215             220
Ile Gly Met Asp Tyr Asp Tyr Ala Leu Leu Glu Leu Lys Lys Pro His
             225             230             235
Lys Arg Lys Phe Met Lys Ile Gly Val Ser Pro Pro Ala Lys Gln Leu
             240             245             250
Pro Gly Gly Arg Ile His Phe Ser Gly Tyr Asp Asn Asp Arg Pro Gly
255             260             265
Asn Leu Val Tyr Arg Phe Cys Asp Val Lys Asp Glu Thr Tyr Asp Leu
270             275             280             285
Leu Tyr Gln Gln Cys Asp Ala Gln Pro Gly Ala Ser Gly Ser Gly Val
             290             295             300
Tyr Val Arg Met Trp Lys Arg Gln Gln Lys Trp Glu Arg Lys Ile
             305             310             315
Ile Gly Ile Phe Ser Gly His Gln Trp Val Asp Met Asn Gly Ser Pro
             320             325             330
Gln Asp Phe Asn Val Ala Val Arg Ile Thr Pro Leu Lys Tyr Ala Gln
             335             340             345
Ile Cys Tyr Trp Ile Lys Gly Asn Tyr Leu Asp Cys Arg Glu Gly
350             355             360
```

SERINE PROTEASE POLYPEPTIDES AND MATERIALS AND METHODS FOR MAKING THEM

CROSS-REFERENCE TO RELATED APPLICATIONS

This application is a continuation-in-part of application Ser. No. 09/062,142, filed Apr. 17, 1998, which application is now abandoned, which claims the benefit of provisional application No. 60/044,185, filed Apr. 24, 1997.

BACKGROUND OF THE INVENTION

Enzymes are used within a wide range of applications in industry, research, and medicine. Through the use of enzymes, industrial processes can be carried out at reduced temperatures and pressures and with less dependence on the use of corrosive or toxic substances. The use of enzymes can thus reduce production costs, energy consumption, and pollution as compared to non-enzymatic products and processes.

An important group of enzymes is the proteases, which cleave proteins. Industrial applications of proteases include food processing, brewing, and alcohol production. Proteases are important components of laundry detergents and other products. Within biological research, proteases are used in purification processes to degrade unwanted proteins. It is often desirable to employ proteases of low specificity or mixtures of more specific proteases to obtain the necessary degree of degradation.

Proteases are also key components of a broad range of biological pathways, including blood coagulation and digestion. For example, the absence or insufficiency of a protease can result in a pathological condition that can be treated by replacement or augmentation therapy. Such therapies include the treatment of hemophilia with clotting factors VIII, IX, and VIIa. In another application, the proteolytic enzyme tissue plasminogen activator (t-PA) is used to activate the body's clot lysing mechanism, thereby reducing morbitity resulting from myocardial infarction. The protease thrombin is used to initiate the clotting of fibrinogen-based tissue adhesives during surgery. Neutrophils produce several antibacterial serine proteases (Gabay, *Ciba Found. Symp.* 186:237–247, 1994; Scocchi et al., *Eur. J. Biochem.* 209:589–595, 1992). Proteases also regulate cellular processes through receptor-mediated pathways by proteolytic activation of the cognate receptor (Vu et al., *Cell* 64:1057–1068, 1991; Blackhart et al., *J. Biol. Chem.* 271:16466–16471, 1996).

Overproduction or lack of regulation of proteases can also have pathological consequences. Elastase, released within the lung in response to the presence of foreign particles, can damage lung tissue if its activity is not tightly regulated. Emphysema in smokers is believed to arise from an imbalance between elastase and its inhibitor, alpha-1-antitrypsin. This balance may be restored by administration of exogenous alpha-1-antitrypsin.

One family of proteases of particular interest is the serine proteases, which are characterized by a catalytic triad of serine, histidine, and aspartic acid residues. Serine proteases are used for a variety of industrial purposes. For example, the serine protease subtilisin is used in laundry detergents to aid in the removal of proteinaceous stains (e.g., Crabb, *ACS Symposium Series* 460:82–94, 1991). In the food processing industry, serine proteases are used to produce protein-rich concentrates from fish and livestock, and in the preparation of dairy products (Kida et al., *Journal of Fermentation and Bioengineering* 80:478–484, 1995; Haard and Simpson, in Martin, A. M., ed., *Fisheries Processing: Biotechnological Applications,* Chapman and Hall, London, 1994, 132–154; Bos et al., European Patent Office Publication 494 149 A1).

In general, enzymes, including proteases, are active over a narrow range of environmental conditions (temperature, pH, etc.), and many are highly specific for particular substrates. The narrow range of activity for a given enzyme limits its applicability and creates a need for a selection of enzymes that (a) have similar activities but are active under different conditions or (b) have different substrates. For instance, an enzyme capable of catalyzing a reaction at 50° C. may be so inefficient at 35° C. that its use at the lower temperature will not be feasible. For this reason, laundry detergents generally contain a selection of proteolytic enzymes, allowing the detergent to be used over a broad range of wash temperature and pH.

In view of the specificity of proteolytic enzymes and the growing use of proteases in industry, research, and medicine, there is an ongoing need in the art for new enzymes and new enzyme inhibitors. The present invention addresses these needs and provides other, related advantages.

SUMMARY OF THE INVENTION

Within one aspect, the present invention provides an isolated protein comprising a sequence of amino acid residues that is at least 95% identical to SEQ ID NO:2 from Ile, residue 111, through Asn, residue 373, wherein the protein is a protease or protease precursor. In one embodiment, the protein has from 254 to 398 amino acid residues. In other embodiments, the protein comprises residues 111 through 373 of SEQ ID NO:2 or SEQ ID NO:15, residues 111 through 364 of SEQ ID NO:18, residues 1 through 373 of SEQ ID NO:2 or SEQ ID NO:15, or residues 1 through 364 of SEQ ID NO:18. The protein can further comprise a heterologous affinity tag or binding domain.

Within a second aspect, the invention provides an isolated polynucleotide up to 1800 nucleotides in length encoding a protein as disclosed above. Within one embodiment, the polynucleotide is DNA. Within another embodiment, the polynucleotide is double-stranded DNA. Within a further embodiment, the protein encoded by the polynucleotide comprises residues −19 through 373 of SEQ ID NO:2.

Within a third aspect, the invention provides an expression vector comprising the following operably linked elements: (a) a transcription promoter; (b) a DNA segment encoding a protein as disclosed above; and (c) a transcription terminator. The expression vector can further comprise a secretory signal sequence operably linked to the DNA segment.

The invention also provides a cultured cell containing an expression vector as disclosed above, wherein the cell expresses the DNA segment. Within one embodiment of the invention the expression vector further comprises a secretory signal sequence operably linked to the DNA segment, and the cell secretes the protein.

There is also provided a method of making a protease or protease precursor. The method comprises the steps of (a) providing a host cell containing an expression vector as disclosed above; (b) culturing the host cell under conditions whereby the DNA segment is expressed; and (c) recovering the protein encoded by the DNA segment. Within one embodiment the expression vector further comprises a secretory signal sequence operably linked to the DNA segment, the cell secretes the protein into a culture medium, and the protein is recovered from the medium.

Within a further aspect of the invention there is provided a method of cleaving a peptide bond of a substrate protein. The method comprises incubating the substrate protein in the presence of a second protein comprising a sequence of amino acid residues that is at least 95% identical to SEQ ID NO:2 from Ile, residue 111, through Asn, residue 373, whereby the peptide bond is cleaved. Within one embodiment, the second protein is a protease precursor and the method further comprises the step of activating the second protein before the peptide bond is cleaved.

The invention further provides a method of detecting an inhibitor of proteolysis within a test sample comprising the steps of (a) measuring proteolytic activity of a protein as disclosed above in the presence of a test sample to obtain a first value; (b) measuring proteolytic activity of the protein in the absence of the test sample to obtain a second value; and (c) comparing the first and second values, whereby a higher second value relative to the first value is indicative of an inhibitor of proteolysis within the test sample.

The invention also provides an antibody that specifically binds to a protein comprising a sequence of amino acid residues that is at least 95% identical to SEQ ID NO:2 from Ile, residue 111, through Asn, residue 373 wherein the protein is a protease or protease precursor.

Within an additional aspect, the invention provides a DNA construct encoding a polypeptide fusion. The polypeptide fusion comprises, from amino terminus to carboxyl terminus, amino acid residues −19 through −1 of SEQ ID NO:2 operably linked to an additional polypeptide.

These and other aspects of the invention will become evident upon reference to the following detailed description of the invention.

DETAILED DESCRIPTION OF THE INVENTION

Prior to setting forth the invention in detail, certain terms used herein will be defined.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term "allelic variant" is also used herein to denote a protein encoded by an allelic variant of a gene.

The term "complements of polynucleotide molecules" denotes polynucleotide molecules having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

A "DNA construct" is a single or double stranded, linear or circular DNA molecule that comprises segments of DNA combined and juxtaposed in a manner not found in nature. DNA constructs exist as a result of human manipulation, and include clones and other copies of manipulated molecules.

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "expression vector" denotes a DNA construct that comprises a segment encoding a polypeptide of interest operably linked to additional segments that provide for its transcription in a host cell. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones, as well as synthetic polynucleotides. Isolated DNA molecules of the present invention may include naturally occurring 5' and 3' untranslated regions such as promoters and terminators. The identification of associated regions will be evident to one of ordinary skill in the art (see for example, Dynan and Tijan, *Nature* 316:774–78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., at least 90% pure, preferably greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term "nucleotides" is used for both single- and double-stranded molecules where the context permits. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

The term "promoter" denotes a portion of a gene containing DNA sequences that provide for the binding of RNA polymerase and initiation of transcription. Promoter sequences are commonly, but not always, found in the 5' non-coding regions of genes.

A "protease" is an enzyme that cleaves peptide bonds in proteins. A "protease precursor" is a relatively inactive form of the enzyme that commonly becomes activated upon cleavage by another protease.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

All references cited herein are incorporated by reference in their entirety.

The present invention provides novel serine proteases, serine protease precursors, and useful polypeptide fragments thereof. The sequence of a representative protein of the present invention is shown in SEQ ID NO:2. This protein shows significant amino acid sequence homology to several serine proteases, including *Bacillus licheniformis* glutamyl endopeptidase (Svendsen and Breddam, *Eur. J. Biochem.* 204:165–171, 1992), human clotting factor X (Leytus et al., *Biochem.* 25:5098–5102, 1986), human elastase (Kawashima et al., *DNA* 6:163–172, 1987), rat mast cell protease (Benfey et al., *J. Biol. Chem.* 262:5377–5384, 1987), *Streptomyces griseus* trypsin (Kim et al., *Biochem. Biophys. Res. Comm.* 181:707–713, 1991), *Hypoderma lineatum* collagenase (*J. Biol. Chem.* 262:7546–7551, 1987), and bovine trypsinogen (Titani et al., *Biochem.* 14:1358–1366, 1975). The protein has been designated "Zsig13".

A Zsig13 polynucleotide sequence was initially identified by querying a database of expressed sequence tags (ESTs) for secretory signal sequences characterized by an upstream methionine start site, a hydrophobic region of approximately 13 amino acid residues, and a cleavage site as defined by von Heijne (*Nuc. Acids Res.* 14:4683, 1986). Analysis of a full-length DNA (shown in SEQ ID NO:1) revealed its homology with other members of the serine protease family. Northern blot analysis indicated the presence of two corresponding messages, a predominant transcript of approximately 1.8 kb and a secondary transcript of approximately 4 kb. The sequence of SEQ ID NO:1 consists of 1634 bp, not including a poly(A) tail. The sequence includes an open reading frame of 1176 base pairs.

An alignment of Zsig13 with related proteins was used to identify the catalytic triad of His (156), Asp (227) and Ser (322) as shown in SEQ ID NO:2. The Leu-Thr-Ala-Ala-His-Cys sequence (residues 152–157 of SEQ ID NO:2) is a characteristic active site His signature within serine proteases. Resides −1 through −19 of SEQ ID NO:2 make up a putative signal peptide. Residues 106–109 of SEQ ID NO:2 (Arg-Arg-Lys-Arg) are a characteristic cleavage site; such cleavage may serve a regulatory function, such as activation of the protein during or after secretion. Activation by proteolytic cleavage is common among serine proteases. While not wishing to be bound by theory, the protein is believed to become active following exposure of a free amino group on Gln 110 or, with additional processing, Ile 111. However, in contrast to many other serine proteases, the non-catalytic, amino-terminal fragment does not appear to remain tethered to the remainder of the molecule after this cleavage has occurred. Alignment of sequences further indicates that active site contact residues are at positions 244 (Ile), 291 (Asp), 292 (Ala), 316 (Lys), 317 (Ile), 328 (Asp), 350 (Ile), 356 (Gly), 358 (Tyr) and 360 (Asp) of SEQ ID NO:2. Sequence alignment identified the Lys residue at position 316 as the key residue in the base of the P1 ligand specificity pocket, generating specificity for Glu and/or Asp in the P1 position of the substrate protein.

With reference to SEQ ID NO:2, additional structural features of Zsig13 include paired cysteine residues at positions 46 and 50, 141 and 157, 276 and 290, and 351 and 361. Potential N-linked glycosylation sites are at residues Asn-74 and Asn-188. The calculated molecular weight of the peptide backbone of the 392-residue precursor is 43,829.55, with a predicted pI of 10.44. The calculated peptide backbone molecular weight of residues 110–373 is 30,074, with a predicted pI of 10.4.

The Zsig13 protein was found to be highly expressed in tissues that are exposed to the external environment, including trachea, bladder, small intestine, colon, and prostate. This tissue distribution suggests a digestive or anti-bacterial function. Several anti-bacterial serine proteases are known to be produced in neutrophils, where they are stored in granules as inactive proforms (Gabay, ibid.; Scocchi et al., ibid.). Expression was also detected in aorta and fetal kidney.

The present invention also provides isolated Zsig13 polypeptides that are substantially homologous to the polypeptides of SEQ ID NO:2 and their orthologs. The term "substantially homologous" is used herein to denote polypeptides having 50%, preferably 60%, more preferably at least 80%, sequence identity to polypeptides of SEQ ID NO:2 or their orthologs. Such polypeptides will more preferably be at least 90% identical, and most preferably 95% or more identical to polypeptides of SEQ ID NO:2 or their orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), thioredoxin, ubiquitin, cellulose binding protein, T7 polymerase, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.; New England Biolabs, Beverly, Mass.). Zsig13 proteins comprising linkers, affinity tags, or other extensions will typically be from 274 to 398 residues in length, given a polypeptide having an amino terminus within residues 1–111 of SEQ ID NO:2 or SEQ ID NO:14 and a carboxyl terminus within residues 364–373 of SEQ ID NO:2 or SEQ ID NO:15, and further comprising an extension of 20–25 residues. Those skilled in the art will recognize that polypeptides comprising longer extensions are also within the scope of the present invention.

TABLE 2

Conservative amino acid substitutions

| | |
|---|---|
| Basic: | arginine |
| | lysine |
| | histidine |
| Acidic: | glutamic acid |
| | aspartic acid |

TABLE 2-continued

Conservative amino acid substitutions

| | |
|---|---|
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occuring amino acid residues. Non-naturally occuring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occuring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occuring amino acid(s) (e.g., 2-azaphenylalanine, 3-azaphenylalanine, 4-azaphenylalanine, or 4-fluorophenylalanine). The non-naturally occuring amino acid is incorporated into the protein in place of its natural counterpart. See, Koide et al., *Biochem.* 33:7470–7476, 1994. Naturally occuring amino acid residues can be converted to non-naturally occuring species by in vitro chemical modification. Chemical modification can be combined with site-directed mutagenesis to further expand the range of substitutions (Wynn and Richards, *Protein Sci.* 2:395–403, 1993).

Essential amino acids in the Zsig13 polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity as disclosed above to identify amino acid residues that are critical to the activity of the molecule. See also, Hilton et al., *J. Biol. Chem.* 271:4699–4708, 1996. Residues important for substrate binding and cleavage can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related serine proteases.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode proteolytically active proteins or precursors thereof can be recovered from the host cells and rapidly sequenced using modern equipment. These methods allow the rapid determination of the importance of individual amino acid residues in a polypeptide of interest, and can be applied to polypeptides of unknown structure.

Using the methods disclosed above, one of ordinary skill in the art can identify and/or prepare a variety of polypeptides that are substantially homologous to residues 111 through 373 of SEQ ID NO:2 or allelic variants thereof and retain the proteolytic properties of the wild-type protein. Such polypeptides may include a targetting moiety comprising additional amino acid residues that form an independently folding binding domain. Such domains include, for example, an extracellular ligand-binding domain (e.g., one or more fibronectin type III domains) of a cytokine receptor; immunoglobulin domains; DNA binding domains (see, e.g., He et al., *Nature* 378:92–96, 1995); affinity tags; and the like. Such polypeptides may also include additional polypeptide segments as generally disclosed above.

In addition to the fusion proteins disclosed above, the present invention provides fusions comprising the secretory peptide of Zsig13 (residues −19 through −1 of SEQ ID NO:2). This secretory peptide can be used to direct the secretion of other proteins of interest by joining a polynucleotide sequence encoding it to the 5' end of a sequence encoding a protein of interest.

Within the present invention, proteins, including variants and fragments of SEQ ID NO:2, can be tested for serine protease activity using conventional assays. Briefly, substrate cleavage is conveniently assayed using a tetrapeptide that mimics the cleavage site of the natural substrate and which is linked, via a peptide bond, to a carboxyl-terminal para-nitro-anilide (pNA) group. The protease hydrolyzes the bond between the fourth amino acid residue and the pNA group, causing the pNA group to undergo a dramatic increase in absorbance at 405 nm. Such substrates will preferably contain a Glu or Asp residue at the P1 position. Suitable substrates can be synthesized according to known methods or obtained from commercial suppliers. When the serine protease is prepared as an inactive precursor (e.g., comprising N-terminal residues 1–109 of SEQ ID NO:2), it is activated by cleavage with a suitable protease (e.g., furin (Steiner et al., *J. Biol. Chem.* 267:23435–23438, 1992)) prior to assay. Assays of this type are well known in the art. See, for example, Lottenberg et al., *Thrombosis Research* 28:313–332, 1982; Cho et al., *Biochem.* 23:644–650, 1984; Foster et al., *Biochem.* 26:7003–7011, 1987).

The isolated polynucleotides of the present invention include DNA and RNA. Methods for isolating DNA and RNA are well known in the art. For example, RNA can be isolated from trachea, bladder, small intestine, colon, or prostate, which RNA is then used as a template for preparation of complementary DNA (cDNA). DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. Polynucleotides encoding Zsig13 polypeptides are then identified and isolated by, for example, hybridization or polymerase chain reaction (PCR).

Within SEQ ID NO:1 and SEQ ID NO:2, residues 80, 95, 96, and 149 can be any amino acid residue (denoted as Xaa). Within a preferred embodiment of the invention, residue 80 is Thr, residue 95 is Gln, residue 96 is His, and residue 149 is Lys.

A second Zsig13 DNA sequence is shown in SEQ ID NO:14 (with the corresponding amino acid sequence shown in SEQ ID NO:15). Within SEQ ID NO:15, residue 60 is Glu, residue 80 is Thr, residue 95 is Gln, residue 96 is His, residue 149 is Lys, residue 299 is Ser, and residue 369 is Pro. All other residues in SEQ ID NO:15 are the same as their respective counterparts in SEQ ID NO:2. The calculated molecular weight of the peptide backbone of the 392-residue polypeptide shown in SEQ ID NO:15 is 43,918.56, with a predicted pI of 10.38. The calculated peptide backbone molecular weight of residues 110–373 is 28,113.80, with a predicted pI of 10.49.

A third Zsig13 DNA sequence is shown in SEQ ID NO:17, with the encoded amino acid sequence shown in SEQ ID NO:18. SEQ ID NO:18 is identical to SEQ ID NO:15, but terminates at residue 364 (Gly) due to a one base pair insertion at position 1256 in SEQ ID NO:17 relative to SEQ ID NO:14. There are two additional differences between SEQ ID NO:14 and SEQ ID NO:17 in the 3' untranslated region (nucleotides 1291 and 1374 of SEQ ID NO:17). The calculated molecular weight of the 383-residue peptide backbone of SEQ ID NO:18 is 43,003.55, with a predicted pI of 10.44. The calculated peptide molecular weight of residues 110–364 is 29,124.01, with a predicted pI of 10.53.

Those skilled in the art will recognize that the sequences disclosed herein are representative of the human Zsig13 gene and polypeptide, and that allelic variation and alternative splicing are expected to occur. Allelic variants can be cloned by probing cDNA or genomic libraries from different individuals according to standard procedures. Allelic variants of the disclosed DNA sequences, including those containing silent mutations and those in which mutations result in amino acid sequence changes, are within the scope of the present invention, as are proteins which are allelic variants of the disclosed protein sequences.

The invention also encompasses degenerate polynucleotide sequences encoding proteins as disclosed above. Those skilled in the art will readily recognize that, in view of the degeneracy of the genetic code, considerable sequence variation is possible among these polynucleotide molecules. SEQ ID NO:16 is a degenerate DNA sequence that encompasses all DNAs that encode the Zsig13 polypeptide of SEQ ID NO:15. Those skilled in the art will recognize that the degenerate sequence of SEQ ID NO:16 also provides all RNA sequences encoding SEQ ID NO:15 by substituting U for T. Thus, Zsig13 polypeptide-encoding polynucleotides comprising segments of SEQ ID NO:16 and their RNA equivalents are contemplated by the present invention. Table 3 sets forth the one-letter codes used within SEQ ID NO:16 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 3

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:16, encompassing all possible codons for a given amino acid, are set forth in Table 4, below.

TABLE 4

| Amino Acid | One-Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR) , and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:15. Variant sequences can be readily tested for functionality as described herein.

For any Zsig13 polypeptide (e.g., SEQ ID NO:18), including variants and fusion proteins, one of ordinary skill in the art can readily generate a fully degenerate polynucleotide sequence encoding that variant using the information set forth in Tables 3 and 4, above.

Allelic variants and orthologs of the human Zsig13 proteins disclosed herein can be obtained by conventional cloning methods. The DNA sequences shown in SEQ ID NO:1, SEQ ID NO:14, SEQ ID NO:17, and portions thereof can be used as probes or primers to prepare other polynucleotides from cells or libraries (including cDNA and genomic libraries) from humans or other animals of interest, particularly mammals including rodents, rabbits, ungulates, primates, and others of economic importance or biomedical interest. It is preferred to derive probes and primers from regions of the molecule that are relatively conserved within the family of serine proteases, such as residues 141–146, 153–158, 209–214, and 224–229 of SEQ ID NO:2. Methods for isolating additional polynucleotides are known in the art. For example, a cDNA can be cloned using mRNA obtained from a tissue or cell type that expresses the protein. Suitable sources of mRNA can be identified by probing Northern blots with probes designed from the sequences disclosed herein. Preferred sources of mRNA include trachea, small intestine, colon, prostate, and bladder. A library is then prepared from mRNA of a positive tissue or cell line. A cDNA of interest can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Of particular interest for cloning are degenerate probes and primers designed from the regions of SEQ ID NO:2 disclosed above and alignment with other serine proteases. Families of preferred degenerate probes are shown in Table 5.

TABLE 5

| Nucleotides (SEQ ID NO: 1) | Sense | Complement |
| --- | --- | --- |
| 582–598 | TGY ACN GGN WSN HTN RT (SEQ ID NO: 3) | AY NAD NSW NCC NGT RCA (SEQ ID NO: 4) |
| 618–634 | ACN GCN GSN CAY TGY AT (SEQ ID NO: 5) | AT RCA RTG NSC NGC NGT (SEQ ID NO: 6) |
| 787–803 | WY RTN CCN WVN GGN TGG (SEQ ID NO: 7) | CCA NCC NBW NGG NAY RW (SEQ ID NO: 8) |
| 831–847 | AYN RAY TAY GAY TAY GS (SEQ ID NO: 9) | SC RTA RTC RTA RTY NRT (SEQ ID NO: 10) |

Within an additional method, the cDNA library can be used to transform or transfect host cells, and expression of the cDNA of interest can be detected with an antibody that specifically binds to an epitope of a Zsig13 polypeptide. Similar techniques can also be applied to the isolation of genomic clones.

Within preferred embodiments of the invention the isolated polynucleotides will hybridize to similar sized regions of SEQ ID NO:1, SEQ ID NO:14, SEQ ID NO:17, or a sequence complementary to SEQ ID NO:1, SEQ ID NO:14, or SEQ ID NO:17, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration does not exceed about 0.03 M at pH 7 and the temperature is at least about 60° C., with washes carried out in the presence of EDTA.

The polypeptides of the present invention, including full-length proteins, fragments thereof, and fusion proteins, are produced in genetically engineered host cells according to conventional techniques. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989.

In general, a DNA sequence encoding a protein of the present invention is operably linked to a transcription promoter and terminator within an expression vector. The vector will commonly contain one or more selectable markers and one or more origins of replication, although those skilled in the art will recognize that within certain systems selectable markers can be provided on separate vectors, and replication of the exogenous DNA can be provided by integration into the host cell genome. Selection of promoters, terminators, selectable markers, vectors and other elements is a matter of routine design within the level of ordinary skill in the art. Many such elements are described in the literature and are available through commercial suppliers.

To direct Zsig13 polypeptides into the secretory pathway of a host cell, a secretory signal sequence (also known as a leader sequence, prepro sequence or pre sequence) is provided in the expression vector. The secretory signal sequence is joined to a DNA sequence encoding a Zsig13 polypeptide in the correct reading frame. Secretory signal sequences are commonly positioned 5' to the DNA sequence encoding the protein of interest, although certain signal sequences may be positioned 3' to the DNA sequence of interest (see, e.g., Welch et al., U.S. Pat. No. 5,037,743; Holland et al., U.S. Pat. No. 5,143,830). The secretory signal sequence of Zsig13 (e.g., the human secretory signal sequence of SEQ ID NO:1 from nucleotide 105 to nucleotide 161) is generally preferred for use in mammalian cells. Signals from host cell genes may be preferred in other types of cells (e.g., yeast cells).

Yeast cells, particularly cells of the genus *Saccharomyces*, are suitable for use within the present invention. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. A preferred vector system for use in yeast is the POT1 vector system disclosed by Kawasaki et al. (U.S. Pat. No. 4,931,373), which allows transformed cells to be selected by growth in glucose-containing media. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica* and *Candida maltosa* are known in the art. See, for example, Gleeson et al., *J. Gen. Microbiol.* 132:3459–3465, 1986; Cregg, U.S. Pat. No. 4,882,279; and Hiep et al., *Yeast* 9:1189–1197, 1993.

The use of *Pichia methanolica* as host for the production of recombinant proteins is disclosed in WIPO Publications WO 97/17450, WO 97/17451, WO 98/02536, and WO 98/02565; and U.S. Pat. No. 5,716,808. DNA molecules for use in transforming *P. methanolica* will commonly be prepared as double-stranded, circular plasmids, which are preferably linearized prior to transformation. For polypeptide production in *P. methanolica,* it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($t$) of from 1 to 40 milliseconds, most preferably about 20 milliseconds.

Other fungal cells are also suitable as host cells. For example, Aspergillus cells can be utilized according to the methods of McKnight et al., U.S. Pat. No. 4,935,349. Methods for transforming *Acremonium chrysogenum* are disclosed by Sumino et al., U.S. Pat. No. 5,162,228.

Cultured mammalian cells can also be used as hosts. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982) and DEAE-dextran mediated transfection (Ausubel et al., eds., *Current Protocols in Molecular Biology*, John Wiley and Sons, Inc., NY, 1987). The production of recombinant proteins in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36:59–72, 1977) cell lines. Additional suitable cell lines are known in the art and available from public depositories such as the American Type Culture Collection, Rockville, Md.

Other higher eukaryotic cells can also be used as hosts, including insect cells, plant cells and avian cells. Transformation of insect cells and production of foreign proteins therein is disclosed by Guarino et al., U.S. Pat. No. 5,162,222 and Bang et al., U.S. Pat. No. 4,775,624. The use of *Agrobacterium rhizogenes* as a vector for expressing genes in plant cells has been reviewed by Sinkar et al., *J. Biosci. (Bangalore)* 11:47–58, 1987.

Prokaryotic host cells for use in carrying out the present invention include strains of the bacteria *Escherichia coli*; Bacillus and other genera are also useful. Techniques for transforming these hosts and expressing foreign DNA sequences cloned therein are well known in the art (see, e.g., Sambrook et al., ibid.). When expressing a Zsig13 protein in bacteria such as *E. coli*, the protein may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured protein can then be then refolded and dimerized by diluting the denaturant, such as by dialysis against a solution of urea and a combination of reduced and oxidized glutathione, followed by dialysis against a buffered saline solution. In the latter case, the protein can be recovered from the periplasmic space in a soluble and functional form by disrupting the cells (by, for example, sonication or osmotic shock) to release the contents of the periplasmic space and recovering the protein, thereby obviating the need for denaturation and refolding.

The secretory peptide of Zsig13 (residues −19 through −1 of SEQ ID NO:2) can be used to direct the secretion of other proteins of interest from a host cell. Such use is within the level of ordinary skill in the art. Briefly, a DNA segment encoding the Zsig13 secretory peptide is operably linked to a second DNA segment encoding a protein of interest within a host cell and the cell is cultured according to conventional methods as summarized below. The protein of interest is then recovered from the culture media.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD.

Recombinant Zsig13 polypeptides (including chimeric polypeptides) can be purified from cells or cell culture media using conventional fractionation and purification methods and media. Ammonium sulfate precipitation and acid or chaotrope extraction may be used for fractionation of samples. Exemplary purification steps include hydroxyapatite, size exclusion, FPLC and reverse-phase high performance liquid chromatography. Suitable anion exchange media include derivatized dextrans, agarose, cellulose, polyacrylamide, specialty silicas, and the like. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports can be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method is a matter of routine design and is determined in part by the properties of the chosen support. See, for example, *Affinity Chromatography: Principles & Methods*, Pharmacia LKB Biotechnology, Uppsala, Sweden, 1988. Activated serine proteases are preferably purified by binding to immobilized p-aminobenzamidine (e.g., Benzamidine-Sepharose®; Pharmacia) with subsequent elution using soluble benzamidine (Winkler et al., *Bio/Technology* 3:990, 1985; Mizuno et al., *Biochem. Biophys. Res. Comm.* 144:807, 1987).

Proteins comprising affinity tags or other binding domains can be purified by exploiting the properties of the additional domain. For example, immobilized metal ion adsorption chromatography (IMAC) can be used to purify histidine-rich proteins, including proteins comprising poly-histidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography ("Guide to Protein Purification", *Methods Enzymol.*, Vol. 182, M. Deutscher, (ed.), Academic Press, San Diego, 1990, pp.529–39).

Zsig13 polypeptides can also be prepared through chemical synthesis. The polypeptides may be glycosylated or non-glycosylated; pegylated or non-pegylated; and may or may not include an initial methionine amino acid residue.

When proteins are produced intracellularly (such as in prokaryotic host cells) or by in vitro synthesis, protein refolding (and optionally reoxidation) procedures as generally disclosed above are advantageously used.

It is preferred to purify Zsig13 proteins to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Proteins of the present invention can be used within laboratory and industrial settings to cleave proteins for a variety of purposes that will be evident to those skilled in the art. The proteins can be used alone to provide specific proteolysis or can be combined with other proteases to provide a "cocktail" with a broad spectrum of activity. Representative laboratory uses include the removal of proteins from biological samples, such as preparations of nucleic acids; and for digesting proteins in conjunction with peptide mapping and sequencing. Within industry, the proteins of the present invention can be formulated in laundry detergents to aid in the removal of protein stains, and can be used within the large scale preparation of recombinant proteins to specifically cleave fusion proteins, including removing affinity tags. The proteins of the present invention can be added to a variety of compositions and solutions as proteolytically active enzymes or as protease precursors. In the latter arrangement, the protein is subsequently activated, such as by the addition of an activating protease.

The proteins of the present invention are also useful as research reagents to identify novel protease inhibitors. Briefly, test samples (compounds, broths, extracts, and the like) are added to protease assays as disclosed above to determine their ability to inhibit substrate cleavage. Inhibitors identified in this way can be used in industry and research to reduce or prevent undesired proteolysis. As with proteases, inhibitors can be combined to increase the spectrum of activity.

Zsig13 proteins and protein fragments can also be used to prepare antibodies that specifically bind to zsig13 proteins. As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies can be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life can be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Alternative techniques for generating or selecting antibodies useful herein include in vitro exposure of lymphocytes to Zsig13 protein, and selection of antibody display libraries in phage or similar vectors (for instance, through use of immobilized or labeled Zsig13 protein). Antibodies are defined to be specifically binding if they bind to a Zsig13 protein with an affinity at least 10-fold greater than the binding affinity to control (non-Zsig13) protein. The affinity of a monoclonal antibody can be readily determined by one of ordinary skill in the art (see, for example, Scatchard, *Ann. NY Acad. Sci.* 51: 660–672, 1949).

Methods for preparing polyclonal and monoclonal antibodies are well known in the art (see for example, Hurrell, J. G. R., Ed., *Monoclonal Hybridoma Antibodies: Techniques and Applications,* CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zsig13 polypeptide can be increased through the use of an adjuvant such as alum (aluminum hydroxide) or Freund's complete or incomplete adjuvant. Polypeptides useful for immunization also include fusion polypeptides, such as fusions of a Zsig13 protein or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

A variety of assays known to those skilled in the art can be utilized to detect antibodies which specifically bind to Zsig13 proteins. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to Zsig13 proteins can be used for affinity purification of the protein, within diagnostic assays for determining circulating levels of the protein; for detecting or quantitating soluble Zsig13 protein or protein fragments as a marker of underlying pathology or disease; for immunolocalization within whole animals or tissue sections, including immunodiagnostic applications; for immunohistochemistry; and as antagonists to block protein activity in vitro and in vivo. Antibodies to Zsig13 can also be used for tagging cells that express Zsig13; for affinity purification of Zsig13 proteins; in analytical methods employing FACS; for screening expression libraries; and for generating anti-idiotypic antibodies. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies of the present invention can also be directly or indirectly conjugated to drugs, toxins, radionuclides and the like, and these conjugates used for in vivo diagnostic or therapeutic applications.

While not wishing to be bound by theory, tissue distribution of Zsig13 mRNA suggests that the protein may play a defensive role. Proteases that serve anitbiotic or antitoxin functions are known (Gabay, ibid.; Scocchi et al., ibid.). Proteins of the present invention may thus be useful as antibiotics and/or antitoxins. They may further be used as diagnostic indicators of infection by assaying body fluids for the presence of Zsig13. Zsig13 proteins or fragments thereof can be detected using, for example, immunoassay techniques employing antibodies specific for Zsig13 epitopes. Assays can be performed using soluble or immobilized antibodies in a variety of known formats.

A Zsig13 gene, a probe comprising Zsig13 DNA or RNA, or a subsequence thereof can be used to determine if the Zsig13 gene is present on chromosome 11 or if a mutation has occurred. Detectable chromosomal aberrations at the Zsig13 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targetted for analysis. For gross analysis of genes, a polynucleotide probe may comprise an entire exon or more. Probes will generally comprise a polynucleotide linked to a signal-generating moiety such as a radionucleotide. In general, gene-based diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, SEQ ID NO:14, or SEQ ID NO:17; the complement of SEQ ID NO:1, SEQ ID NO:14, or SEQ ID NO:17; or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; A. J. Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–38, 1991).

Radiation hybrid mapping is a somatic cell genetic technique developed for constructing high-resolution, contiguous maps of mammalian chromosomes (Cox et al., *Science* 250:245–250, 1990). Partial or full knowledge of a gene's sequence allows one to design PCR primers suitable for use with chromosomal radiation hybrid mapping panels. Commercially available radiation hybrid mapping panels that cover the entire human genome, such as the Stanford G3 RH Panel and the GeneBridge 4 RH Panel (Research Genetics, Inc., Huntsville, Ala.), are available. These panels enable rapid, PCR-based chromosomal localizations and ordering of genes, sequence-tagged sites (STSs), and other nonpolymorphic and polymorphic markers within a region of interest. This technique allows one to establish directly proportional physical distances between newly discovered genes of interest and previously mapped markers. The precise knowledge of a gene's position can be useful for a number of purposes, including: 1) determining relationships between short sequences and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The invention is further illustrated by the following, non-limiting examples.

EXAMPLE 1

Tissue distribution of Zsig13 mRNA was analyzed using Human Multiple Tissue Northern Blots (obtained from Clontech, Inc., Palo Alto, Calif.). A 40-bp DNA probe (ZC 11,667; SEQ ID NO:11) was radioactively labeled with $^{32}P$ using T4 polynucleotide kinase and forward reaction buffer (GIBCO BRL, Gaithersburg, Md.) according to the supplier's specifications. The probe was purified using a push column (Nuctrap™ column; Stratagene Cloning Systems, La Jolla, Calif.). Prehybridization and hybridization were carried out in a commercially available solution (ExpressHyb™ hybridization solution; Clontech Laboratories, Inc., Palo Alto, Calif.). Blots were hybridized overnight at 42° C., washed in 2× SSC, 0.05% SDS at room temperature, then in 1× SSC, 0.1% SDS at 60° C. Two transcripts were observed: a strongly hybridizing ~1.8 kb band and a fainter band at approximately 4.0 kb.

An RNA Master Dot Blot (Clontech Laboratories) that contained RNAs from various tissues that were normalized to eight housekeeping genes was also probed with the 40-bp oligonucleotide probe (SEQ ID NO:11). The blot was prehybridized, then hybridized overnight with $10^6$ cpm/ml of probe of 42° C. according to the manufacturer's specifications. The blot was washed with 2× SSC, 0.05% SDS at room temperature, then in 1× SSC, 0.1% SDS at 60° C. After a four-day exposure, signals were seen in trachea, aorta, bladder, and fetal kidney.

EXAMPLE 2

Zsig13 was mapped to chromosome 11 using the commercially available GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research (WICGR) radiation hybrid map of the human genome, which was constructed with the GeneBridge 4 Radiation Hybrid Panel.

For the mapping of Zsig13, 20 µl reaction mixtures were set up in a PCRable 96-well microtiter plate (Stratagene Cloning Systems, La Jolla, Calif.) and incubated in a thermal cycler (RoboCycler™ Gradient 96; Stratagene Cloning Systems). Each of the 95 PCR reactions consisted of 2 µl 10× KlenTaq PCR reaction buffer (Clontech Laboratories, Inc.), 1.6 µl dNTPs mix (2.5 mM each, Perkin-Elmer, Foster City, Calif.), 1 µl sense primer (ZC 13,508; SEQ ID NO:12), 1 µl antisense primer (ZC 13,509; SEQ ID NO:13), 2 µl of a commercially available density increasing agent and tracking dye (RediLoad; Research Genetics, Inc., Huntsville, Ala.), 0.4 µl of polymerase/antibody mixture (50× Advantage™ KlenTaq Polymerase Mix; Clontech Laboratories, Inc.), 25 ng of DNA from an individual hybrid clone or control and ddH$_2$O for a total volume of 20 µl. The reaction mixtures were overlaid with an equal amount of mineral oil and sealed. The PCR cycler conditions were as follows: an initial 5 minute denaturation at 95° C.; 35 cycles of a 1 minute denaturation at 95° C., 1 minute annealing at 62° C. and 1.5 minute extension at 72° C.; followed by a final extension of 7 minutes at 72° C. The reaction products were separated by electrophoresis on a 3% NuSieve® GTG agarose gel (FMC Bioproducts, Rockland, Me.).

The results showed that Zsig13 maps 417.10 cR_3000 distal from the top of the human chromosome 11 linkage group on the WICGR radiation hybrid map. Proximal and distal framework markers were D11S1979 and D11S2384, respectively. The use of surrounding markers positions Zsig13 in the 11q22.1 region on the integrated LDB chromosome 11 map (The Genetic Location Database, University of Southhampton, www server: http://cedar.genetics.soton.ac.uk/public_html/). This region of chromosome 11 is fairly rich in proteases.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. An isolated protein comprising residues 111 through 373 of SEQ ID NO:2, residues 111 through 373 of SEQ ID NO:15, or residues 111 through 364 of SEQ ID NO:18.

2. The isolated protein of claim 1 having from 254 to 398 amino acid residues.

3. The isolated protein of claim 1 wherein said protein comprises residues 111 through 364 of SEQ ID NO:18.

4. The isolated protein of claim 1 comprising residues 1 through 364 of SEQ ID NO:18.

5. The isolated protein of claim 1 comprising residues 1 through 373 of SEQ ID NO:2 or SEQ ID NO:15.

6. The isolated protein of claim 1 comprising residues 111 through 373 of SEQ ID NO:2.

7. The isolated protein of claim 1 comprising residues 111 through 373 of SEQ ID NO:15.

8. The isolated protein of claim 1, further comprising a heterologous affinity tag or binding domain.

9. An isolated polynucleotide up to 1800 nucleotides in length, said polynucleotide encoding a protein comprising residues 111 through 373 of SEQ ID NO:2, residues 111 through 373 of SEQ ID NO:15, or residues 111 through 364 of SEQ ID NO:18.

10. The isolated polynucleotide of claim 9 which is DNA.

11. The isolated polynucleotide of claim 10 wherein said DNA is double-stranded.

12. The isolated polynucleotide of claim 9 wherein said protein comprises residues −19 through 373 of SEQ ID NO:2 or SEQ ID NO:15.

13. The isolated polynucleotide of claim 9 wherein said protein comprises residues −19 through 364 of SEQ ID NO:18.

14. An expression vector comprising the following operably linked elements:

a transcription promoter;

a DNA segment encoding a protein comprising residues 111 through 373 of SEQ ID NO:2, residues 111 through 373 of SEQ ID NO:15, or residues 111 through 364 of SEQ ID NO:18; and a transcription terminator.

15. The expression vector of claim 14 wherein said protein comprises residues 111 through 373 of SEQ ID NO:2 or SEQ ID NO:15.

16. The expression vector of claim 14 wherein said protein comprises residues 111 through 364 of SEQ ID NO:18.

17. The expression vector of claim 14 wherein said protein comprises residues 1 through 373 of SEQ ID NO:2 or SEQ ID NO:15.

18. The expression vector of claim 14 wherein said protein comprises residues 1 through 364 of SEQ ID NO:18.

19. The expression vector of claim 14 further comprising a secretory signal sequence operably linked to said DNA segment.

20. The expression vector of claim 19 wherein said secretory signal sequence encodes amino acid residues −19 through −1 of SEQ ID NO:2.

21. A cultured cell containing an expression vector according to claim 14 wherein said cell expresses said DNA segment.

22. The cultured cell of claim 21 wherein the expression vector further comprises a secretory signal sequence operably linked to said DNA segment and the cell secretes said protein.

23. A method of making a protease or protease precursor comprising:

(a) providing a host cell containing an expression vector comprising the following operably linked elements:

(i) a transcription promoter;

(ii) a DNA segment encoding a protein comprising residues 1 through 373 of SEQ ID NO:2, residues 1 through 373 of SEQ ID NO:15, or residues 1 through 364 of SEQ ID NO:18; and (iii) a transcription terminator, whereby said cell expresses said DNA segment;

(b) culturing said host cell under conditions whereby said DNA segment is expressed; and (c) recovering the protein encoded by said DNA segment.

24. The method of claim 23 wherein the expression vector further comprises a secretory signal sequence operably linked to said DNA segment, the cell secretes the protein into a culture medium, and the protein is recovered from the medium.

* * * * *